United States Patent [19]

Crump

[11] 4,185,094

[45] Jan. 22, 1980

[54] BIOCIDAL COMPOSITION

[75] Inventor: Ronald A. Crump, Horsham, England

[73] Assignee: The British Petroleum Company Limited, London, England

[21] Appl. No.: 830,314

[22] Filed: Sep. 2, 1977

[30] Foreign Application Priority Data

Sep. 9, 1976 [GB] United Kingdom ............... 37377/76

[51] Int. Cl.$^2$ .......................... B05D 3/02; B32B 9/04; A01N 9/00; A01N 9/24
[52] U.S. Cl. ................................ 424/172; 106/18.29; 106/243; 106/270; 106/271; 114/67 R; 260/406; 260/410.9 R; 424/288; 260/410.6; 427/388 C; 260/427.7; 427/416
[58] Field of Search ............... 427/385 R, 388 C, 416; 106/15 R, 18, 243, 270, 271, 18.29; 428/484; 144/67 R; 260/406, 410 R; 424/172, 288

[56] References Cited

U.S. PATENT DOCUMENTS 4,020,200  4/1977  Groszek et al. ...................... 427/416

FOREIGN PATENT DOCUMENTS 1479701  7/1977  United Kingdom ..................... 427/385
1479702  7/1977  United Kingdom ..................... 427/385

*Primary Examiner*—Michael R. Lusignan
*Attorney, Agent, or Firm*—Morgan, Finnegan, Pine, Foley & Lee

[57] ABSTRACT

Wax coatings for underwater surfaces, e.g. ship's hulls, contain as biocidal component, an organo-tin ester (preferably a tribydrocarbyl tin ester) of an oxidized wax or an aliphatic fatty acid.

The oxidized wax may be an oxidized petroleum wax and the fatty acid a $C_{12}$–$C_{30}$ acid. The ester may form 5–100% of the finished coating and the other wax component, if present, may be a conventional petroleum wax.

11 Claims, No Drawings

BIOCIDAL COMPOSITION

This invention relates to anti-fouling compositions suitable for preventing marine growth on underwater surfaces, and particularly to the biocidal compositions used therein.

The coating of surfaces intended for underwater use with wax to reduce roughness, corrosion and fouling has already been proposed. Thus U.K. Pat. No. 1,336,103 discloses the use of a wax coating as a temporary protective for ships' hulls and U.K. Pat. No. 1,441,611 extends this concept to more permanent protection having a life of at least one year. Our U.K. Pat. No. 1,479,701 is concerned with applying a wax coating in the form of an aqueous emulsion or dispersion and our U.K. Pat. No. 1,479,702 discloses that the wax coatings may contain a biocide.

In choosing the most suitable biocide a number of factors have to be taken into account.

Firstly, the biocide or its effective component should be released from the coating into the water in a steady, controlled fashion so that the coating has a long effective life as regards anti-fouling. It is generally accepted that anti-fouling paints have room for improvement in this respect. For example, E. J. Dyckman et al commented in an article in the Naval Engineers Journal, December 1973, pages 33 to 37 that "anti-fouling paint formulations containing e.g. tributyl tin oxide still leach these agents at a rate in excess of the lethal concentration needed for fouling prevention", and in the Australian OCCA Proceedings and News, July 1973, page 17, A. T. Phillip said "It is thought that tributyltin oxide behaves like a solvent and diffuses rapidly to the surface of the film so that, after an initial period of effectiveness, its activity falls off with time".

One solution to the problem has been to put a so-called "self-polishing coating" over the top of a conventional anti-fouling paint. The self-polishing coating contains a polyester of an acrylic acid and an organo-tin compound e.g. tri-alkyl tin compound. The ester gradually hydrolyses releasing organo-tin oxide into the water and the coating is steadily worn away in the process.

These self polishing coatings although effective, are nevertheless relatively expensive.

Secondly, the biocide should be fully compatible with the other components of the coating. In the context of wax coatings this means that the biocide itself should be compatible with wax as should any residue left over when the active component of the biocide is released. If the wax coating is applied as an aqueous emulsion it also means that the biocide should not adversely affect the formation or the stability of the emulsion.

Thirdly, the biocide should be as inexpensive as possible consistent with acceptable quality.

The present invention is concerned with the use of organo-tin esters which are based on relatively cheap acids and which are compatible with wax coatings.

According to the present invention film-forming wax composition suitable for use as a marine anti-fouling coating contains a organo-tin ester of an oxidised wax or an aliphatic fatty acid.

The organo-tin radical of the ester may be of general formula $R_3Sn-$

Where R is a hydrocarbyl group. R preferably has from 1 to 10 carbon atoms and may be alkyl e.g. propyl or butyl, cycloalkyl or aryl, e.g. phenyl.

As described in more detail hereafter, the ester may be formed by reacting the oxidised wax or aliphatic fatty acid with an organo-tin compound of general formula $R_3Sn\ X$ 

Where R is as indicated above and X is an anion.

The term "oxidised wax" means any wax, either synthetic or natural, which contains carboxylic acid or anhydride groups capable of being esterified with an organo-tin compound and/or which contains ester groups capable of ester exchange with an organo-tin compound.

A preferred starting material for the production of oxidised wax is the mineral wax obtained from petroleum fractions boiling above 300° C. by well-known solvent dewaxing techniques. The waxes consist primarily of paraffin hydrocarbons and these may be normal-paraffins (the so-called crystalline waxes derived from distillate petroleum fractions) or iso-paraffins (the so-called microcrystalline waxes derived from brightstock or residual petroleum fractions). The waxes normally have melting points of from 45° to 120° C. and molecular weights of at least 300.

Carboxylic acid groups may be introduced into paraffin waxes by oxidation with an oxygen containing gas, usually air, at moderately elevated temperatures of about 100°–200° C. and usually in the presence of a catalyst. The gas may be blown through the molten wax as small bubbles (e.g. by using a sintered disc as the gas inlet). The pressure is normally atmospheric, though elevated pressures may be used. A variety of oxidation catalysts may be used, those most commonly used being compounds of manganese, cobalt, copper, iron, or silver. The metal compounds may be oxides or salts, particularly salts of organic acids such as fatty acids, and the catalyst may be dissolved or suspended in the molten wax.

Other waxes that may be susceptible to oxidation are waxes produced by the Fischer-Tropsch synthesis of carbon monoxide and hydrogen and polyolefin waxes, e.g. polyethylene or polypropylene waxes, which may have molecular weights in the range 5,000 to 15,000.

Naturally occurring vegetable and animal waxes may also be suitable as starting material for the production of organo-tin esters. Some may already contain oxygen and be susceptible to esterification and/or ester group exchange. For example Carnauba wax, a wax originating from the leaves of Brazilian palms, contains about 85% of esters. Candelilla wax may also be suitable.

An alternative to the use of oxidised wax esters is, as previously indicated, the use of esters of aliphatic fatty acids. The fatty acids may have from 12 to 30 carbon atoms and may be saturated or unsaturated. Examples of suitable acids include stearic, oleic, palmitic, lauric and linoleic acids. Commercially available mixtures of fatty acids may also be used e.g. the material sold as Alox 600 by the Alox Corporation.

The reaction of the organo-tin compound and the oxidised wax or fatty acid to give the ester may be carried out quite simply by heating the reactants under reflux in a suitable solvent e.g. benzene. Water produced by the reaction may be taken off overhead e.g. as an azeotrope with benzene and measured to monitor the course of the reaction. Stoichiometric amounts of the reactants may be used and the reaction allowed to go to completion.

It should be readily apparent that the esters used in the present invention have the previously mentioned characteristics required for a biocide to be used in wax coatings. Being esters, they should give controlled release of the active trihydrocarbyl tin component by hydrolysis. Also, the esters themselves are compatible with wax and the residues remaining after hydrolysis are equally compatible. Finally the esters can be made from readily available and relatively inexpensive components.

Oxidised waxes may have acid values of from 5 to 200 mg KOH/g and a wax with an acid value of 50 can be esterified to incorporate 0.26 g of trialkyl tin/g of ester when the tin compound is tributyl tin oxide. Exchange of ester groups if the oxidised wax contains such groups may increase the trihydrocarbyl tin content even higher. Aliphatic fatty acids can be esterified to give substantially molar amounts of trialkyl tin in the ester.

The wax compositions of the present invention should, as previously indicated, be film forming and in the case of oxidised wax esters it is possible for the composition to consist entirely of the ester. However, at the levels of trihydrocarbyl tin content of the esters which are possible, it is preferred to mix the esters with other types of wax, and such mixing with wax will clearly be necessary with the fatty acid esters.

The wax compositions may contain from 2 to 20% by weight of organo-tin groups e.g. trihydrocarbyl tin, by weight of the finished coating and such levels may be obtained by the incorporation of from 5 to 100% wt, preferably from 10 to 50% wt, of ester in the finished coating.

The wax used in the compositions of the present invention may have a melting point of from 45° to 120° C. and a penetration of from 1 to 60mm/10 as measured by ASTM D1 321. For convenience, the wax is preferably predominantly mineral wax derived from a petroleum fraction boiling above 300° C. e.g. n-paraffin (crystalline) or isoparaffin (micro-crystalline) wax, but minor amounts of other waxes may be present to assist in obtaining the required qualities of hardness, gloss, and plasticity e.g. chlorinated or non-esterified oxidised wax, Montan wax, ozokerite, ceresine, Carnauba wax, polyolefin wax or Fischer-Tropsch wax.

The thickness of the finished coating may be from 5 to 500 micrometers, preferably from 50 to 400 micrometers, control being achieved by the rate of application and the viscosity of the composition as applied.

The invention is illustrated by the following examples.

EXAMPLE 1

Tributyl tin stearate was prepared by refluxing 59.5 6 (0.1 mole) tributyl tin oxide
56.8 g (0.2 mole) stearic acid
200 ml benzene The reaction was continued until 1.8 ml of water had been collected overhead indicating complete reaction.

EXAMPLE 2

Triphenyl tin stearate was produced using the method of Example 1, the reactants being 0.1 mole triphenyl tin hydroxide and 0.1 mole stearic acid in 200 ml of benzene.

EXAMPLE 3

The tributyl tin ester of an oxidised wax was prepared using 35 g oxidised paraffin wax
20 g tributyl tin oxide
100 ml benzene The mixture was refluxed for 3 hours and the reaction was complete as measured by the amount of water collected overhead.

The oxidised wax was prepared as follows:

Using manganese naphthanate (1% on wax) as catalyst, oxygen was bubbled through paraffin wax (of 60°/62° C. melting point) at 130° C. for 3 hours. The oxidised wax had an acid value of 106 mg KOH/g.

EXAMPLE 4

The esters of Examples 1 and 2 were incorporated into cationic wax emulsions having the following compositions.

| | | |
|---|---|---|
| Paraffin Wax (60/62° C. melting point) | 120 g | 120 g |
| Laurylamine | 5 g | 5 g |
| Conc. HCl | 3 g | 3 g |
| Cetyl Alcohol | 5 g | 7.5 g |
| Dioctylphthalate | 2 g | 2 g |
| White Spirit | 5 g | 5 g |
| Water | 140 g | 147.5 g |
| Tin Compound | 20 g (Tributyl tin Stearate) | 10 g (triphenyl tin Stearate) |

The emulsions were sprayed onto 2 inch by 7 inch mild steel plates covered with an anti-corrosive primer paint. The wax coatings contained 12.5% wt of tributyl tin stearate by weight of finished coating (of which 6.8% wt was tributyl tin) and 7% wt of triphenyl tin stearate (of which 4.1% wt was triphenyl tin). The plates were immersed in sea water at two locations. The tributyl tin stearate plate was immersed on a gas platform 45 miles out in the southern North Sea. Significant resistance to marine growth was observed after 3 months exposure. Control plates with no anti-fouling agent were covered with hydroid growth after the same time.

The triphenyl tin stearate plate was immersed in Singapore harbour for 6 weeks. A complete absence of marine fouling was observed. Control plates having wax coatings containing no anti-fouling agents were completely covered in barnacle growth after the same time.

EXAMPLE 5

The tributyl tin wax ester of Example 3 was incorporated into a cationic wax emulsion having the following composition.

| | |
|---|---|
| Paraffin wax (60/62° C. melting point) | 100 g |
| Cetyl Alcohol | 7.5 g |
| Di-Octyl phthalate | 2 g |
| Laurylamine | 5 g |
| Conc. HCl | 3 g |
| White Spirit | 5 g |
| Tributyl tin - wax ester | 10 g |

| -continued | |
|---|---|
| Water | 167.5 g |

An emulsion was obtained by heating the above components at 85° C. and stirring vigorously with a Silverson mixer. The emulsion was cooled to below 30° C. with stirring and stored in screw-topped glass bottles.

This emulsion was sprayed onto a 2 inch by 7 inch mild steel plate covered with anti-corrosive primer paint. The wax coating contained 7.5% wt of tributyl tin wax ester by weight of finished coating (of which 2.7% wt was tributyl tin). The plate was immersed in Singapore harbour for 6 weeks. After 6 weeks immersion, the plate was completely free of marine fouling. A control plate having a wax coating formed from the same wax emulsion but containing no tin compound was heavily barnacle fouled after the same time.

I claim:

1. A film-forming wax composition containing from 2 to 20% by wt of organo-tin groups by weight of finished coating suitable for use as a marine anti-fouling coating containing an organo-tin ester of an oxidised wax or a aliphatic fatty acid, wherein the organo-tin radical of the ester having the formula $$R_3Sn-$$

where R is a hydrocarbyl group having from 1 to 10 carbon atoms selected from the group consisting of alkyl, cyclo-alkyl and aryl groups.

2. A film-forming wax composition as claimed in claim 1 wherein there is provided a second wax component besides the oxidized wax ester, said second wax component having a melting point of 45° C. to 120° C.

3. A method of protecting an underwater surface from marine fouling comprising coating the surface with a film of a film-forming wax composition as claimed in claim 1.

4. A film-forming wax composition as claimed in claim 1 wherein the oxidised wax is obtained by oxidation of wax obtained from a petroleum fraction boiling above 300° C.

5. A film-forming wax composition as claimed in claim 1 wherein the oxidised wax has an acid value of from 5 to 200 mg KOH/g.

6. A film-forming wax composition as claimed in claim 1 wherein the aliphatic fatty acid has from 12 to 30 carbon atoms.

7. A film-forming wax composition as claimed in claim 1 which contains from 5 to 100% of ester by weight of finished coating.

8. A film-forming wax composition as claimed in claim 7 which contains from 10 to 50% wt of ester by weight of finished coating.

9. A film-forming wax composition as claimed in claim 2 wherein the second wax component is a mineral wax derived from a petroleum fraction boiling above 300° C.

10. A method as claimed in claim 3 wherein the coating has a thickness of from 5 to 500 micrometers.

11. A method as claimed in claim 9 wherein the coating is applied as an aqueous emulsion.

* * * * *